United States Patent
Komarnycky (10) Patent No.: US 7,481,314 B2
(45) Date of Patent: Jan. 27, 2009

(54) PACKAGING ASSEMBLY FOR SURGICAL MESH IMPLANTS

(75) Inventor: Peter Komarnycky, Lebabon, NJ (US)

(73) Assignee: Ethicon, Inc., Somerville, NJ (US)

( * ) Notice: Subject to any disclaimer, the term of this patent is extended or adjusted under 35 U.S.C. 154(b) by 681 days.

(21) Appl. No.: 11/049,508

(22) Filed: Feb. 2, 2005

(65) Prior Publication Data

US 2006/0196788 A1    Sep. 7, 2006

(51) Int. Cl.
B65D 83/00 (2006.01)
B65D 75/20 (2006.01)
A61B 17/04 (2006.01)

(52) U.S. Cl. .................. 206/438; 206/363; 206/339

(58) Field of Classification Search ............... 206/440, 206/438, 570, 363, 339; 606/151
See application file for complete search history.

(56) References Cited

U.S. PATENT DOCUMENTS

| | | | |
|---|---|---|---|
| 3,182,662 | A | 5/1965 | Schirodkar |
| 3,212,502 | A | 10/1965 | Myers |
| 3,311,110 | A | 3/1967 | Singerman |
| 3,372,695 | A | 3/1968 | Beliveau et al. |
| 3,472,232 | A | 10/1969 | Earl |
| 3,608,095 | A | 9/1971 | Barry |
| 3,763,860 | A | 10/1973 | Clarke |
| 3,858,783 | A | 1/1975 | Kapitanov et al. |
| 3,924,633 | A | 12/1975 | Cook et al. |
| 4,037,603 | A | 7/1977 | Wendorff |
| 4,128,100 | A | 12/1978 | Wendorff |
| 4,235,238 | A | 11/1980 | Ogiu et al. |
| 4,279,344 | A | 7/1981 | Holloway |
| 4,392,495 | A | 7/1983 | Bayers |
| 4,441,497 | A | 4/1984 | Paudler |
| 4,509,516 | A | 4/1985 | Richmond |

(Continued)

FOREIGN PATENT DOCUMENTS

AU    278089 B    6/1965

(Continued)

OTHER PUBLICATIONS

Leanza, V. et al. New Technique For Correcting Both Incontinence And Cystocele: T.I.C.T. (Tension-Free Incontinence Cystocele Treatment) Urogynaecologia International Journal, 2001, No. 3515, pp. 133-140.

(Continued)

Primary Examiner—Mickey Yu
Assistant Examiner—Steven A. Reynolds (57) ABSTRACT

A package assembly for surgical mesh including a carrier assembly including a first substantially flat, flexible protective element having a periphery and positioned in a first plane, and a second substantially flat, flexible protective element having a periphery and positioned in second plane parallel and substantially adjacent to the first plane; and a substantially flat, flexible surgical mesh having first and second sides and positioned between the first and second protective elements. The first and second protective elements are further dimensioned to substantially cover the first and second sides of the surgical mesh respectively. The first and second protective elements are joined together along at least a portion of their respective peripheries, but along no more of the periphery than that which will allow the first and second protective elements to be separated from one another to allow removal of the mesh by a user without separating the joined portion of their peripheries.

7 Claims, 8 Drawing Sheets

U.S. PATENT DOCUMENTS

| | | | |
|---|---|---|---|
| 4,549,545 A | 10/1985 | Levy | |
| 4,736,746 A | 4/1988 | Anderson | |
| 4,930,674 A | 6/1990 | Barak | |
| 4,946,467 A | 8/1990 | Ohi et al. | |
| 5,013,292 A | 5/1991 | Lemay | |
| 5,032,508 A | 7/1991 | Naughton et al. | |
| 5,080,667 A | 1/1992 | Chen et al. | |
| 5,112,344 A | 5/1992 | Petros | |
| 5,180,385 A | 1/1993 | Sontag | |
| 5,219,077 A * | 6/1993 | Transue | 206/438 |
| 5,249,682 A * | 10/1993 | Transue | 206/438 |
| 5,250,033 A | 10/1993 | Evans et al. | |
| 5,281,237 A | 1/1994 | Gimpelson | |
| 5,337,736 A | 8/1994 | Reddy | |
| 5,361,782 A | 11/1994 | Bauer | |
| 5,362,294 A | 11/1994 | Seitzinger | |
| 5,368,595 A | 11/1994 | Lewis | |
| 5,368,756 A | 11/1994 | Vogel et al. | |
| 5,370,294 A | 12/1994 | Bauer | |
| 5,382,257 A | 1/1995 | Lewis et al. | |
| 5,383,904 A | 1/1995 | Totakura et al. | |
| 5,403,328 A | 4/1995 | Shallmam | |
| 5,441,508 A | 8/1995 | Gazielly et al. | |
| 5,450,860 A | 9/1995 | O'Connor | |
| 5,503,638 A | 4/1996 | Cooper et al. | |
| 5,507,796 A | 4/1996 | Hasson | |
| 5,520,700 A | 5/1996 | Beyar et al. | |
| 5,540,240 A | 7/1996 | Bauer | |
| 5,582,188 A | 12/1996 | Benderev et al. | |
| 5,611,515 A | 3/1997 | Benderev et al. | |
| 5,628,756 A | 5/1997 | Barker, Jr. et al. | |
| 5,645,568 A | 7/1997 | Chervitz et al. | |
| 5,741,299 A | 4/1998 | Rudt | |
| 5,755,728 A | 5/1998 | Maki et al. | |
| 5,807,403 A | 9/1998 | Beyar et al. | |
| 5,816,258 A | 10/1998 | Jervis | |
| 5,836,315 A | 11/1998 | Benderev et al. | |
| 5,840,011 A | 11/1998 | Landgrebe et al. | |
| 5,855,549 A | 1/1999 | Newman | |
| 5,860,425 A | 1/1999 | Benderev et al. | |
| 5,899,909 A | 5/1999 | Claren et al. | |
| 5,899,999 A | 5/1999 | De Bonet | |
| 5,934,283 A | 8/1999 | Willem et al. | |
| 5,935,122 A | 8/1999 | Fourkas et al. | |
| 5,945,122 A | 8/1999 | Abra et al. | |
| 5,972,000 A | 10/1999 | Beyar | |
| 5,972,008 A | 10/1999 | Kalinski et al. | |
| 5,997,554 A | 12/1999 | Thompson | |
| 6,010,447 A | 1/2000 | Kardjian | |
| 6,030,393 A | 2/2000 | Corlew | |
| 6,042,534 A | 3/2000 | Gellman et al. | |
| 6,042,536 A | 3/2000 | Tihon et al. | |
| 6,068,591 A | 5/2000 | Bruckner et al. | |
| 6,110,101 A | 8/2000 | Tihon et al. | |
| 6,117,067 A | 9/2000 | Gil-Vernet | |
| 6,190,401 B1 | 2/2001 | Green et al. | |
| 6,197,036 B1 | 3/2001 | Tripp et al. | |
| 6,221,005 B1 | 4/2001 | Bruckner et al. | |
| 6,273,852 B1 | 8/2001 | Lehe et al. | |
| 6,306,079 B1 | 10/2001 | Trabucco | |
| 6,334,446 B1 | 1/2002 | Beyar | |
| 6,382,214 B1 | 5/2002 | Raz et al. | |
| 6,406,423 B1 | 6/2002 | Scetbon | |
| 6,475,139 B1 | 11/2002 | Miller | |
| 6,478,727 B2 | 11/2002 | Scetbon | |
| 6,491,703 B1 | 12/2002 | Ulmsten | |
| 6,494,887 B1 | 12/2002 | Kaladelfos | |
| 6,517,932 B1 | 2/2003 | Peiffer et al. | |
| 6,575,897 B1 | 6/2003 | Ory et al. | |
| 6,575,984 B2 | 6/2003 | Beyar | |
| 6,575,998 B2 | 6/2003 | Beyar | |
| 6,592,610 B2 | 7/2003 | Beyar | |
| 6,595,911 B2 | 7/2003 | LoVuolo | |
| 6,605,097 B1 | 8/2003 | Lehe et al. | |
| 6,612,977 B2 | 9/2003 | Staskin et al. | |
| 6,652,450 B2 | 11/2003 | Neisz et al. | |
| 6,691,711 B2 | 2/2004 | Raz et al. | |
| 6,692,506 B1 | 2/2004 | Ory et al. | |
| 6,802,807 B2 | 10/2004 | Anderson et al. | |
| 6,808,486 B1 | 10/2004 | O'Donnell | |
| 6,808,487 B2 | 10/2004 | Migliari | |
| 6,830,052 B2 | 12/2004 | Carter et al. | |
| 7,243,791 B2 * | 7/2007 | Detruit et al. | 206/363 |
| 2001/0018549 A1 | 8/2001 | Scetbon | |
| 2001/0049467 A1 | 12/2001 | Lehe et al. | |
| 2002/0028980 A1 | 3/2002 | Thierfelder et al. | |
| 2002/0058959 A1 | 5/2002 | Gellman | |
| 2002/0077526 A1 | 6/2002 | Kammerer et al. | |
| 2002/0091373 A1 | 7/2002 | Berger | |
| 2002/0099258 A1 | 7/2002 | Staskin et al. | |
| 2002/0099259 A1 | 7/2002 | Anderson et al. | |
| 2002/0107430 A1 | 8/2002 | Neisz et al. | |
| 2002/0147382 A1 | 10/2002 | Neisz et al. | |
| 2002/0151762 A1 | 10/2002 | Rocheleau et al. | |
| 2002/0161382 A1 | 10/2002 | Niesz et al. | |
| 2002/0188169 A1 | 12/2002 | Kammerer et al. | |
| 2003/0023137 A1 | 1/2003 | Gellman | |
| 2003/0023138 A1 | 1/2003 | Luscombe | |
| 2003/0036676 A1 | 2/2003 | Scetbon | |
| 2003/0050530 A1 | 3/2003 | Neisz et al. | |
| 2003/0062052 A1 | 4/2003 | Carter et al. | |
| 2003/0078468 A1 | 4/2003 | Skiba et al. | |
| 2003/0149440 A1 | 8/2003 | Kammerer et al. | |
| 2003/0171644 A1 | 9/2003 | Anderson et al. | |
| 2003/0176762 A1 | 9/2003 | Kammerer | |
| 2003/0176875 A1 | 9/2003 | Anderson et al. | |
| 2003/0191360 A1 | 10/2003 | Browning | |
| 2003/0195386 A1 | 10/2003 | Thierfelder et al. | |
| 2003/0212305 A1 | 11/2003 | Anderson et al. | |
| 2003/0220538 A1 | 11/2003 | Jacquetin | |
| 2004/0015048 A1 | 1/2004 | Neisz et al. | |
| 2004/0039453 A1 | 2/2004 | Anderson et al. | |
| 2004/0068159 A1 | 4/2004 | Neisz et al. | |
| 2004/0106845 A1 | 6/2004 | Anderson et al. | |
| 2004/0161561 A1 | 8/2004 | Kawamura et al. | |
| 2004/0225181 A1 | 11/2004 | Chu et al. | |
| 2004/0243166 A1 | 12/2004 | Odermatt et al. | |
| 2004/0249240 A1 | 12/2004 | Goldman et al. | |
| 2004/0249397 A1 | 12/2004 | Delorme et al. | |
| 2005/0098460 A1 * | 5/2005 | Smith et al. | 206/366 |

FOREIGN PATENT DOCUMENTS

| | | |
|---|---|---|
| AU | 441561 B | 1/1972 |
| DE | 4334419 A1 | 4/1995 |
| EP | 0 556 018 A | 8/1993 |
| EP | 0 579 377 A | 1/1994 |
| EP | 0 598 976 A2 | 6/1994 |
| EP | 0 774 240 B1 | 5/1997 |
| EP | 0941712 A1 | 9/1999 |
| EP | 1025811 A | 8/2000 |
| GB | 1 602 834 A | 11/1981 |
| SE | 503271 C2 | 4/1996 |
| WO | WO 90/03766 A1 | 4/1990 |
| WO | WO 96/06567 A1 | 3/1996 |
| WO | WO 96/06597 | 3/1996 |
| WO | WO 97/13465 | 4/1997 |
| WO | WO 98/31301 A1 | 7/1998 |
| WO | WO 99/11195 A | 3/1999 |
| WO | WO 01/06951 A1 | 2/2001 |
| WO | WO 02/38079 | 5/2002 |

WO    WO 2004/012626 A1    2/2004

OTHER PUBLICATIONS

Collinet, P., et al., "The Vaginal Patch For Vaginal Cure Of Cystocele", J. Gynecol. Obstet. Biol. Reprod./vol. 29, No. 2, 2000, pp. 197-201.

Cosson, M. et al., "Cystocele Repair By Vaginal Patch", , Progres en Urologie, 2001, 11, pp. 340-346.

Petros, P.E. Papa, "Vault Prolapse II:Restoration of Dynamic Vaginal Supports by Infracoccygeal Sacropexy, an Axial Day-Case Vaginal Procedure". International Urogynecol Journal (2001) vol. 12, pp. 296-303, Springer-Verlag London Ltd.

Petros, P.E. Papa, "Vault Prolapse 1: Dynamic Supports of the Vagina", International Urogynecol Journal (2001) vol. 12, pp. 292-295, Springer-Verlag London Ltd.

"AMS Sparc™ Sling System", American Medical Systems, Inc., Minnetonka, MN, 2001, pp. 1-7.

"TVT Tension-free Vaginal Tape, Minimally Invasive Highly Effective Treatment for Female Stress Urinary Incontinence", Gynecare, Ethicon, Inc., 1999, pp. 1-6.

U.S. Appl. No. 10/941,241, filed Sep. 15, 2004.

* cited by examiner

PACKAGING ASSEMBLY FOR SURGICAL MESH IMPLANTS

FIELD OF THE INVENTION

This invention relates generally to the field of packaging of medical implants, and more specifically to a package assembly that is particularly suitable for use in packaging surgical meshes.

DESCRIPTION OF THE PRIOR ART

Figure 1A:
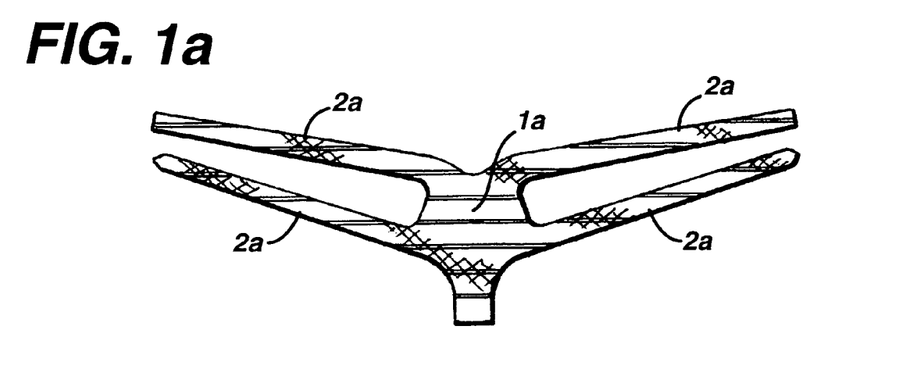
FIGS. 1a-1c illustrate exemplary meshes for use in pelvic floor repair procedures.
Figure 1B:
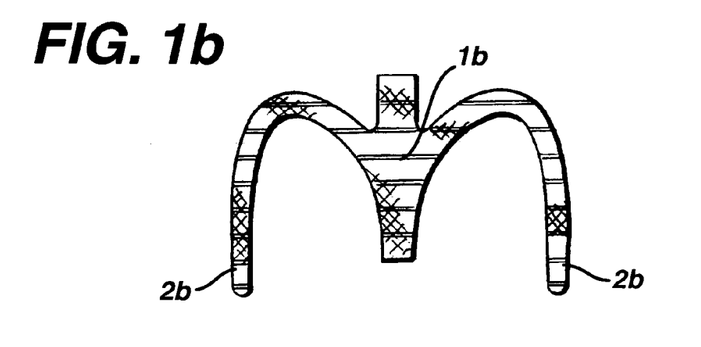
Figure 1C:
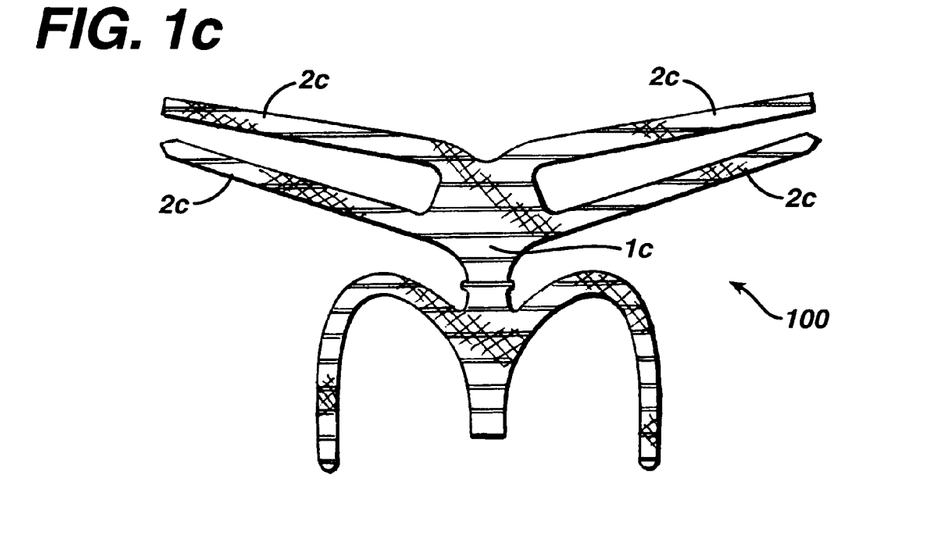

Surgical meshes have widespread use in various surgical procedures. One particular application is for use in supporting prolapsed organs in pelvic floor repair procedures. For example, meshes can be used to restore to a normal position and support a prolapsed bladder to treat a condition known as cystocele, or to support a prolapsed rectum to treat a condition known as rectocele. Different mesh configurations have been used, some of which are set forth in U.S. patent publication no. 2003/0220538, and co-pending U.S. patent application Ser. No. 10/941,241, which are incorporated herein by reference in their entirety. Exemplary mesh 100 configurations are set forth in FIGS. 1a through 1c, where FIG. 1a illustrates one embodiment of a mesh designed for use in cystocele repair, FIG. 1b illustrates one embodiment of a mesh designed for use in rectocele repair, and FIG. 1c illustrates one embodiment of a combination mesh that can be used for both cystocele and rectocele repair. As is described in greater detail in U.S. patent application Ser. No. 10/941,241, the central portions 1a, 1b, 1c of the meshes typically are positioned beneath the prolapsed organ, whereas the strip portions 2a, 2b, 2c extend outwardly away from the central portion and, through tissue ingrowth or alternative securing means (such as stapling, tacking, stitching or the like), provide support for the prolapsed organ via the central portion.

Often times a surgeon will have to treat more than one condition, and thus may require more than one mesh configuration, or may prefer an alternative mesh configuration suitable for treating both conditions such as that shown in FIG. 1c. Further, because patients so greatly vary in size, it is typically necessary for the surgeon to alter the mesh, such as by cutting the length of the strip portions, so that the mesh will properly fit the particular patient. Given these mesh variations, it is most efficient and economical if a single package can be offered to accommodate most, or all, of such meshes, and if that package is conducive to further alteration of the mesh without compromising sterility.

With regard to sterility, it is also important that a package enable the product to be presented into the sterile surgical environment in a simple and efficient manner. Known surgical mesh packages typically position the mesh within some type of sealed container or pouch with the mesh being situated between a bottom package element and a top package element that is sealed with the bottom package element. To open the package, the user must physically separate the top element from the bottom element, usually requiring the separation of two, three, or even four edges. Thus, the steps involved to access the surgical mesh at the time it is needed are cumbersome and time consuming. Further, since the mesh is typically further cut or altered by the surgeon before implantation, this type of packaging requires complete removal of the mesh from its packaging before it can be altered.

Some attempts have been made to reduce the size of the package for surgical meshes by folding the mesh prior to placing it in a package. Tight folds, however, tend to create creases in the mesh, which are disadvantageous in many surgical procedures since the fold lines can cause irritation to surrounding tissue.

In addition to the mesh itself, specific surgical instruments are often provided to facilitate implantation of a particular mesh for a particular application. For example, the surgical instruments described in co-pending U.S. patent application Ser. No. 10/941,241 are particularly suited for implantation of the meshes shown in FIGS. 1a-1c. Thus, it is often desirable to provide a kit including instrumentation and meshes for certain surgical procedures such as pelvic floor repair.

Accordingly, what is needed is improved packaging assembly for packaging surgical meshes, and/or for packaging surgical meshes in combination with surgical instruments that facilitate implantation of the meshes.

OBJECTS AND SUMMARY OF THE INVENTION

The present invention provides a package assembly for surgical mesh including a carrier assembly including a first substantially flat, flexible protective element having a periphery and positioned in a first plane, and a second substantially flat, flexible protective element having a periphery and positioned in second plane parallel and substantially adjacent to the first plane. The assembly further includes a substantially flat, flexible surgical mesh having first and second sides and positioned between the first and second protective elements, wherein the first and second protective elements are further dimensioned to substantially cover the first and second sides of the surgical mesh respectively. The first and second protective elements are joined together along at least a portion of their respective peripheries, but along no more of the periphery than that which will allow the first and second protective elements to be separated from one another to allow removal of the mesh by a user without separating the joined portion of their peripheries. The peripheries of the first and second protective elements may each include a first substantially straight edge, with the first and second protective elements being joined together along said first edges. The peripheries of the first and second protective elements may further be substantially identical. In yet another embodiment, the peripheries of the first and second protective elements each include a second substantially straight edge that is substantially parallel to the first side edge.

In an alternate embodiment, the peripheries of the first and second protective elements each define an area including a first area portion and a second area portion, wherein the first area portion is adjacent to the first edge, and the second area portion is adjacent to the first area portion and on an opposite side of the first area portion from the first edge, and wherein the first area portion has a width greater than that of the second area portion. The surgical mesh may further include a first mesh portion having a first width and a second mesh portion having a second width less than the first width. The first mesh portion is positioned between the first area portions of the protective elements and the second mesh portion is positioned between the second area portions of the protective elements. In yet another embodiment, the first and second protective elements are joined together only along their first edges.

The first protective element may optionally be made of a transparent or translucent material, which may be a copolymer polypropylene or polyester clear or translucent film. The second protective element may optionally be made of Tyvek®.

In one embodiment of the package assembly, the surgical mesh is a mesh for pelvic floor repair.

The package assembly may further include at least one surgical instrument for use in implanting said surgical mesh, a container for receiving therein the at least one surgical instrument, and the surgical mesh and carrier assembly combination. The container has an open top side, a bottom side, and at least one sidewall, wherein the bottom side and at least one sidewall define an internal area within the container. The assembly further includes a divider element positioned within the container so as to divide the internal area into a first portion adjacent the bottom side and a second portion adjacent the open top side. The surgical mesh and carrier assembly combination are positioned within the first internal area portion, and the surgical instruments are positioned on the divider element and within the second internal area portion. The combination surgical mesh and carrier assembly may be loosely folded prior to positioning within the first internal area portion of the container.

The present invention also provides a method for packaging a surgical mesh including providing a first substantially flat, flexible protective element having a periphery, providing a second substantially flat, flexible protective element having a periphery, providing a substantially flat, flexible surgical mesh having first and second sides, positioning the first and second protective elements in substantially parallel and adjacent planes and joining them together along a portion of their respective peripheries, and inserting the mesh between the first and second protective elements so that the first and second sides of the mesh are substantially covered by the first and second protective elements. The portion of the periphery joined in the joining step is sufficient to hold the first and second protective elements together, but allow separation of the first and second protective elements from one another to enable removal of the mesh without separation of the joined portion of their peripheries.

The method may further include the providing at least one surgical instrument for implanting the surgical mesh, providing a container having a bottom side, an open top side, and at least one sidewall, wherein the bottom side and at least one sidewall define an internal area within the container, loosely folding the combination mesh and protective elements, placing the folded combination into the container, placing a divider element within the container and above the folded combination, placing the at least one surgical instrument on the divider element, and sealing the open top side of the container.

A package for a surgical mesh is also provided that includes first and second substantially flat, flexible protective elements each having a substantially identical periphery that includes a first substantially straight edge and a second substantially straight edge substantially parallel to the first substantially straight edge. The first and second protective elements are positioned in substantially parallel planes and substantially adjacent to one another, and the first and second protective elements are joined with one another only along their respective first substantially straight edges. According to one embodiment, the first substantially straight edge of the first and second protective elements has a length that is greater than a length of the second substantially straight edge.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

Although the present invention is described in detail in conjunction with surgical meshes particularly suitable for treating pelvic floor defects, it is to be understood that the invention is not so limited, as there are numerous other types and configurations of meshes for various applications that could be used in connection with the invention described herein.

As indicated previously, FIGS. 1a-1c illustrate exemplary embodiments of meshes for pelvic floor repair procedures. FIGS. 2-6 illustrate an exemplary package assembly according to the present invention including such meshes (or any other surgical meshes). As shown best in FIGS. 2 and 3, a carrier assembly 200 includes a first protective element 202 and a second protective element 204. Both the first and second protective elements are preferably substantially flat, flexible elements each defined by their respective peripheries 206, 208. In a preferred embodiment, the first protective element is comprised of a transparent or translucent material, such as a copolymer film sheet made from Polypropylene or Polyester, and the second protective element is comprised of spun bound polyethylene fibrous sheet such as Tyvek®.

Figure 3:
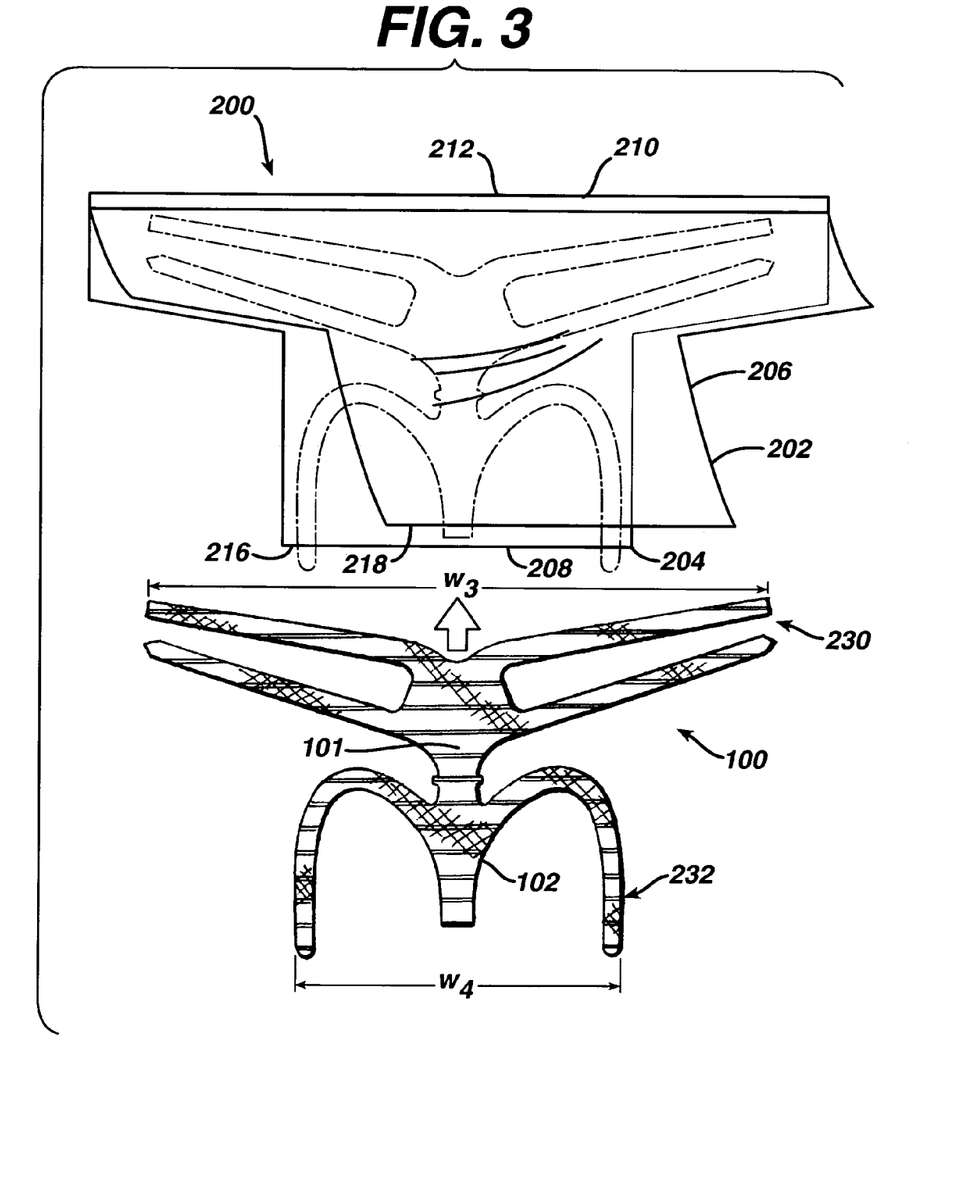
FIG. 3-6 illustrate insertion of the mesh of FIG. 2 within the carrier assembly of FIG. 2, and further steps for manipulating thereof.

The first and second protective elements are positioned substantially adjacent to one another and in substantially parallel planes. By substantially adjacent what is meant is that they are positioned close to one another and perhaps touching at points, but far enough to allow insertion therebetween of a surgical mesh as shown in FIG. 3. The first and second protective elements are joined to one another along at least a portion of their respective peripheries. In the illustrated exemplary embodiment, the first and second protective elements each have a first substantially straight edge 210, 212 having a length x, which forms the portion 214 (the joining portion) of the periphery along which they are joined together. Although the joining portion 214 may have various other configurations (i.e, not a substantially straight edge) or various lengths, what is important is that it be less than the entire periphery, and along no more of the length of the periphery to enable the mesh to be inserted therein, and later removed therefrom (see FIG. 3) without requiring physical separation of the joining portion.

The features described above provide numerous advantages over known prior art packaging for surgical meshes. First, the carrier assembly provides a simple an effective protective barrier for the mesh while still allowing further handling or manipulation of the mesh. For example, once in the carrier assembly, the mesh can be protected while it is further sterilized and/or transferred into another package for sterilization. In addition, during a surgical procedure the carrier assembly can be handled by a user without direct contact with the mesh. The flat, flexible protective elements can also be readily cut, enabling a user to alter the mesh prior to use without direct handling of the mesh. Finally, removal of the mesh from the carrier assembly is greatly simplified, as elements of the carrier need not be separated from one another to remove the mesh.

As indicated, the mesh can be properly sterilized even after it has been placed within the carrier assembly. In the preferred embodiment, the first protective element is preferably made of a Copolymer Polypropylene or Polyester film, whereas the second protective element is preferably made of Tyvek®. These materials, along with the existence of open portion(s) of the periphery as described above, allow a mesh positioned therebetween to be sterilized by typical gas sterilization processes such as by ethylene oxide exposure.

Figure 2:
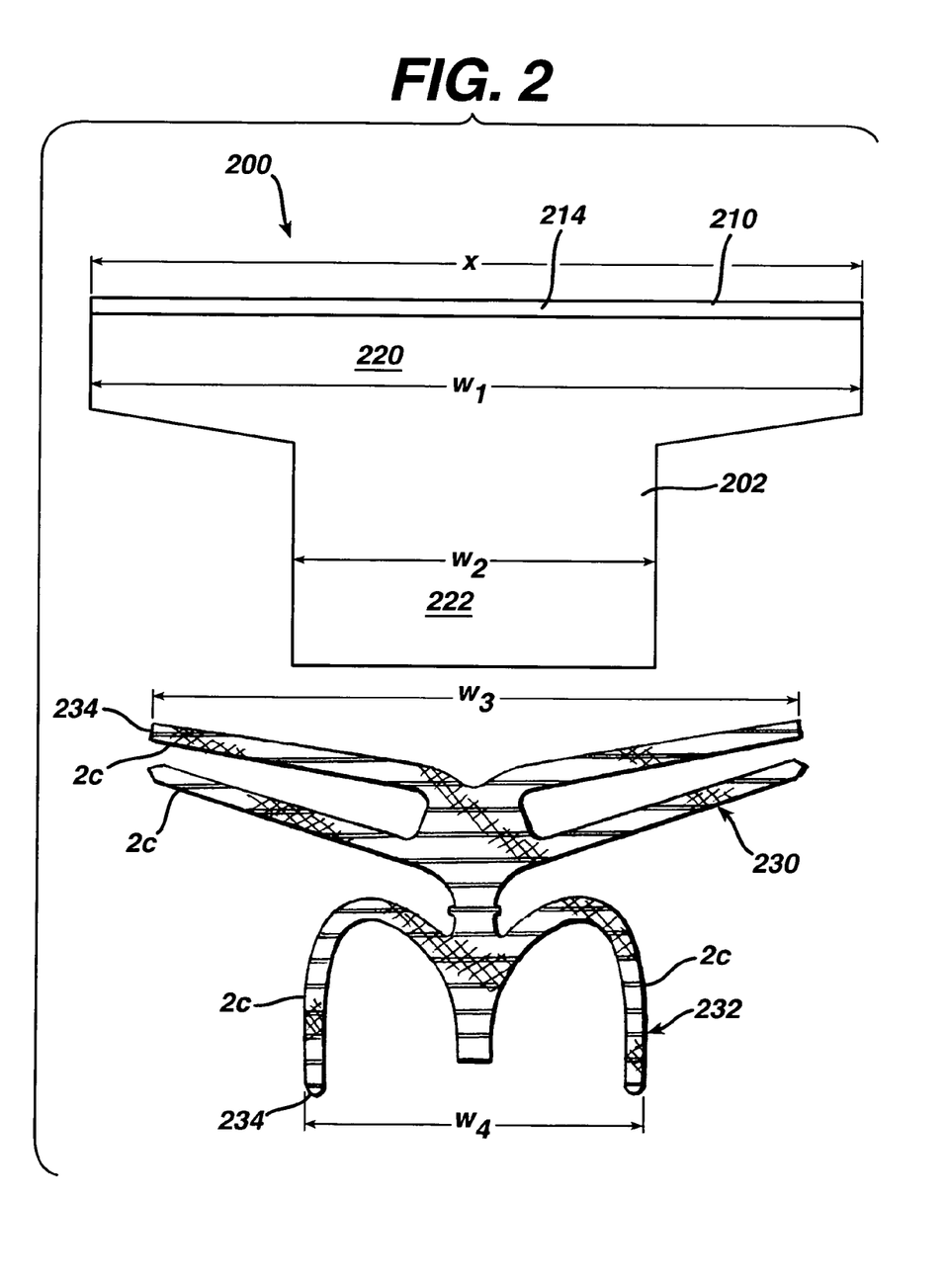
FIG. 2 illustrates an exemplary surgical mesh and exemplary carrier assembly.

In the illustrated embodiment, which is particularly suited for receiving pelvic floor repair meshes, the first and second protective elements of the carrier assembly have substantially identical peripheries, and each further include a second straight edge 216, 218 that is opposite and substantially parallel to, but shorter in length than, the first straight edge 210, 212. The peripheries define an area including a first area portion 220 having a first width $w_1$ and a second area portion 222 having a second width $w_2$ that is less than the first width $w_1$. The first area portion is adjacent to the first edge, and the second area portion adjacent the second edge. The mesh 100 also includes a first mesh portion 230 having a first width $w_3$ and a second mesh portion 232 having a second width $W_4$ that is less than the first width. The widths $w_1$, $w_2$ of the protective elements relative to the widths $w_3$, $w_4$ of the mesh portions should be such that when the mesh is inserted into the carrier assembly, first and second sides of the mesh 101, 102 should be substantially covered by the first and second protective elements. The mesh is considered substantially covered even if distal portions of the mesh, such as the distal portions 234 of the strips portions 2c of mesh 100, are not entirely covered by the protective elements.

Figure 7:
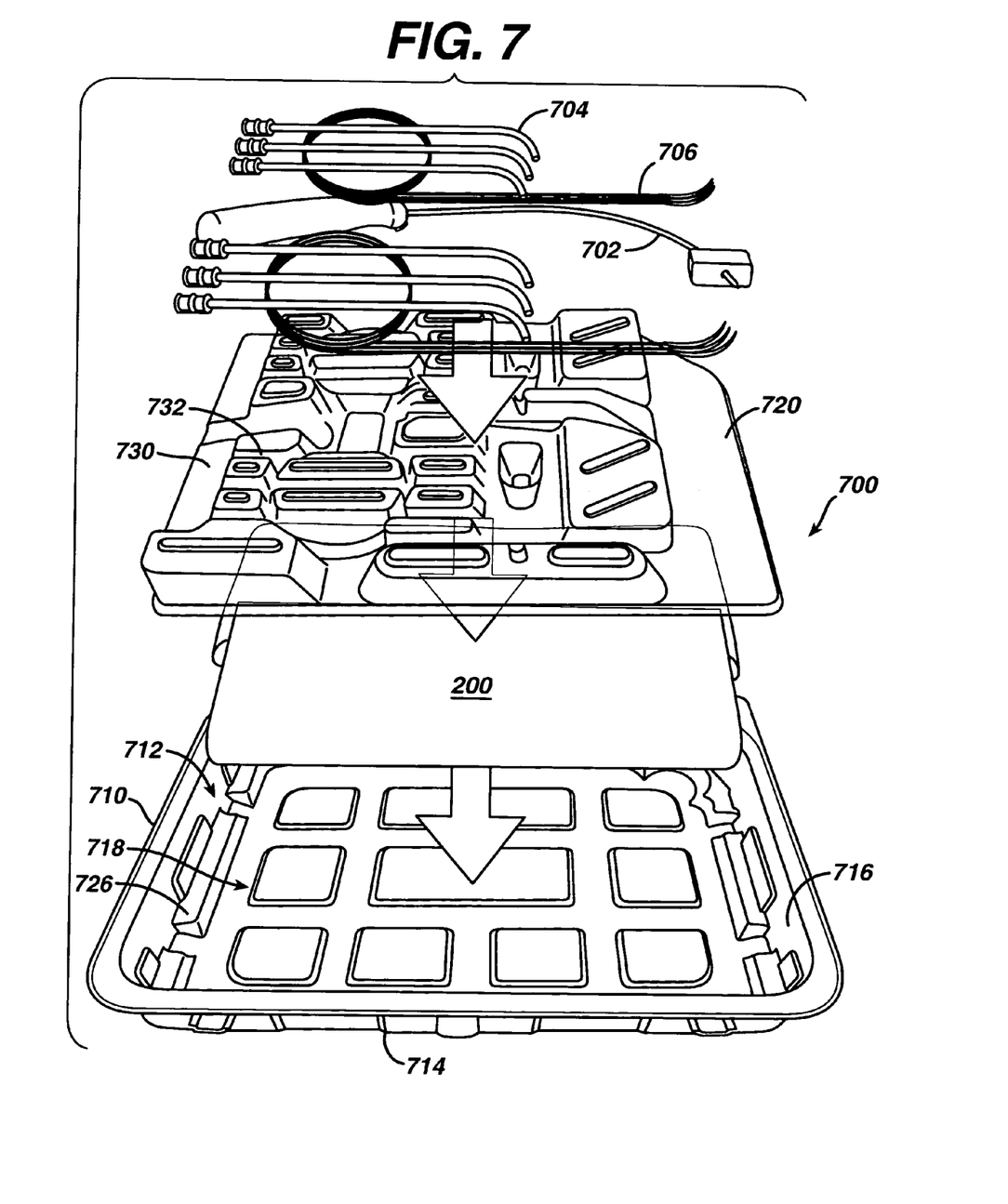
FIG. 7 is an exploded view of an exemplary package assembly including surgical instruments and a carrier assembly.
Figure 8:
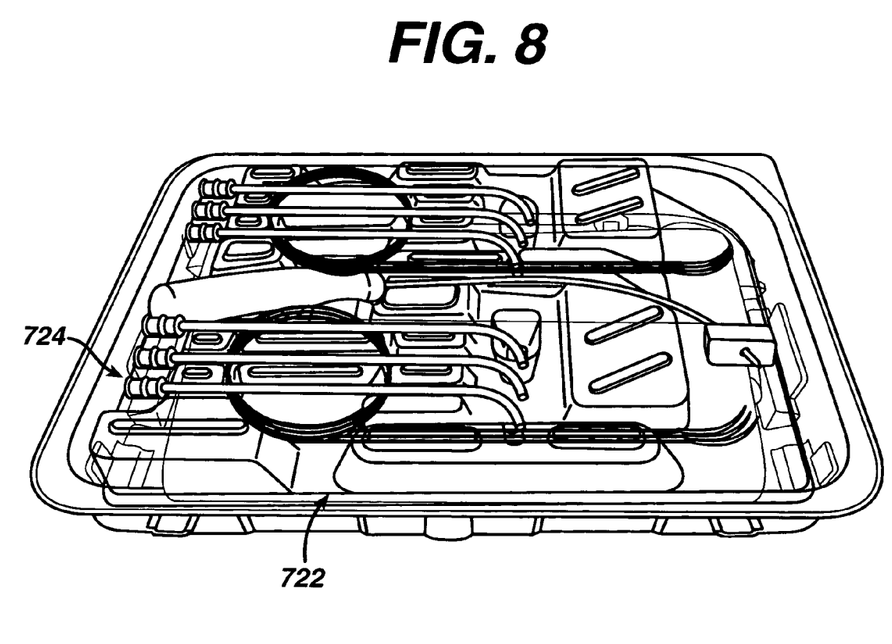
FIG. 8 is a perspective view of the package assembly of FIG. 7.

As previously stated, it is often convenient to provide in a single package, both the surgical mesh and one or more surgical instruments that are particularly suited to facilitate implantation of the mesh. FIG. 7 illustrates exemplary surgical instruments that can be used to implant the mesh 100, including a needle-like element 702, a cannula 704 and a retrieval line 706. These instruments and their use are described in detail in co-pending U.S. application Ser. No. 10/941,241. To accommodate both the mesh and surgical instruments, a package assembly 700 according to the present invention is provided. The package assembly includes a container 710 for receiving therein at least one surgical instrument and a mesh. The container has an open top side 712, a bottom side 714, and at least one sidewall 716, wherein the bottom and sidewall together define an internal area 718 within the container. The package assembly further includes a divider element 720 that, when positioned within the container, divides the internal area 718 into a first area portion 722 between the divider element and the bottom side, and a second area portion 724 between the divider element and the open top side. In the illustrated embodiment shown in FIG. 7, the package assembly further includes one or more protrusions 726 extending inwardly from the sidewall 716 into the internal area 718. The divider element is dimensioned such that it fits within the sidewall, but rests upon the protrusions. Although this particular embodiment is illustrated and described, those skilled in the art will recognize numerous other ways in which a divider element in conjunction with the container results in first and second area portions within the container. For example, the sidewall may be tapered inwardly from top to bottom, and the width of the divider element made such that it fits snugly within the container part way down the sidewall.

Figure 4:
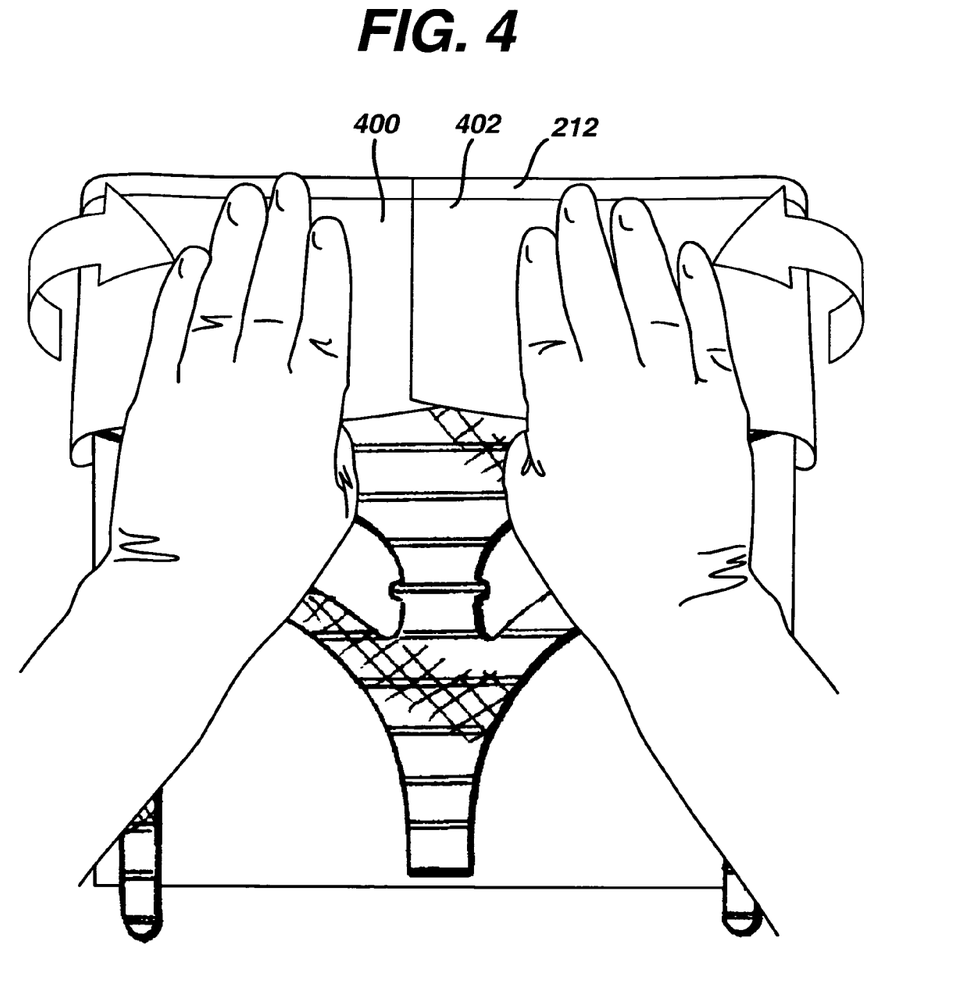
Figure 5:
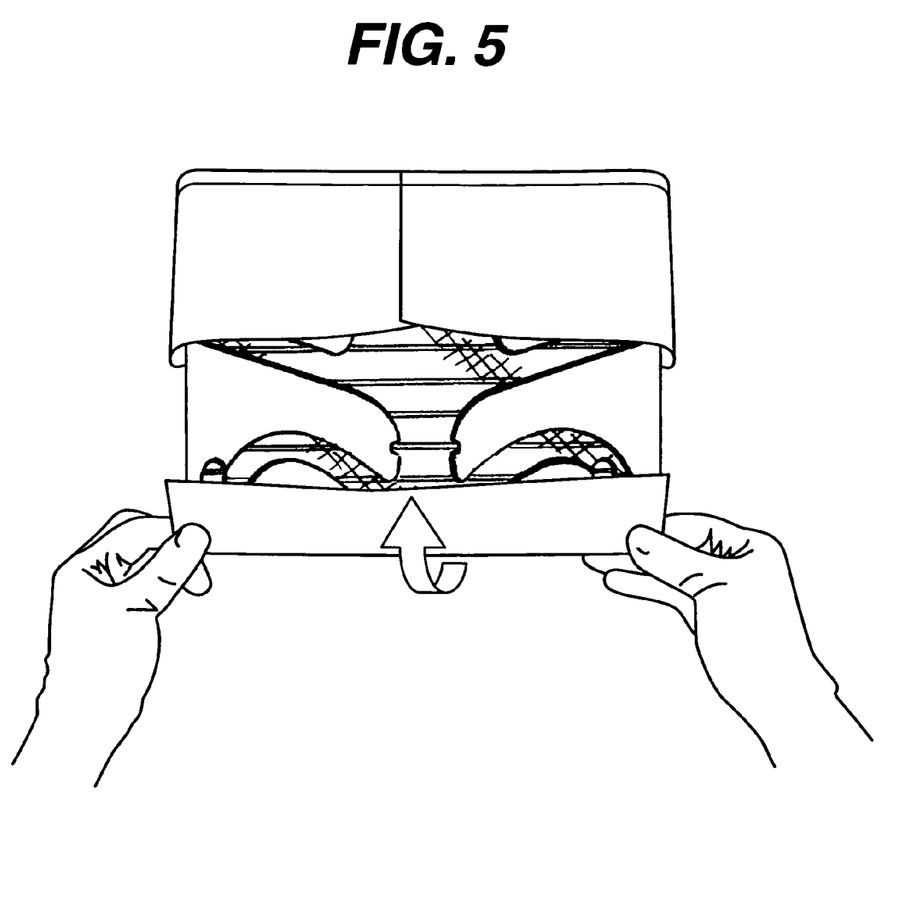
Figure 6:
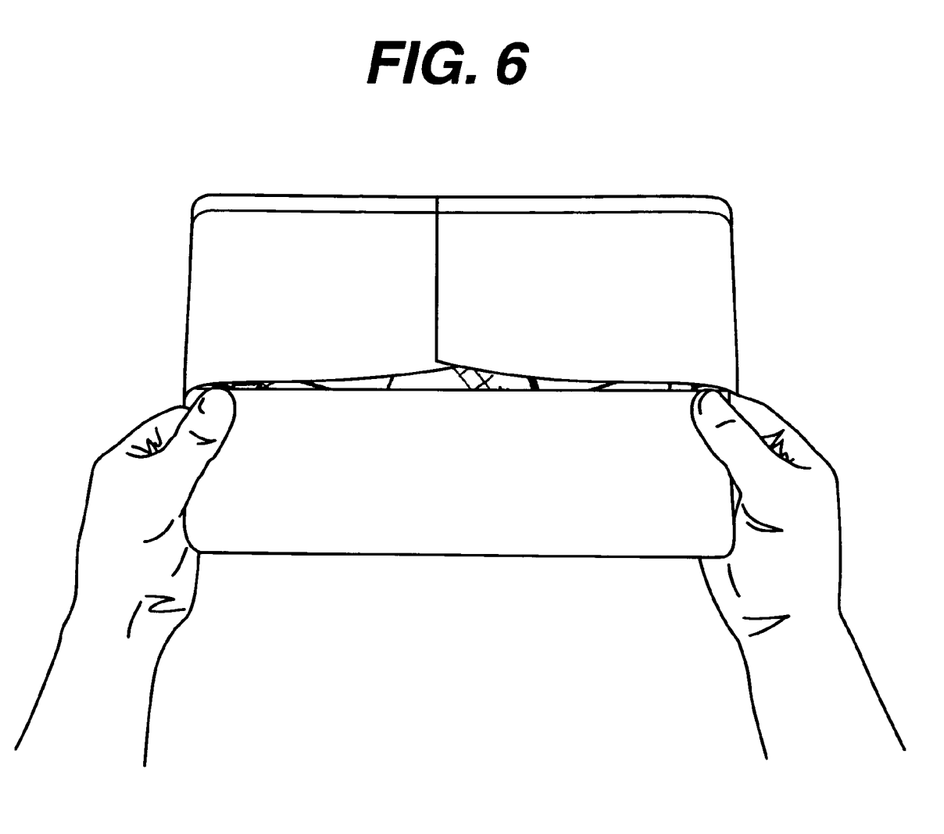

The divider element may further have a suitable configuration so that the at least one surgical instrument can be received and held in place in the top side 730 of the divider element. To accomplish this the divider element may be comprised of molded plastic or the like, with any variation of protrusions and or recesses 732 dimensioned to receive specific surgical instrument(s). Referring back to FIGS. 4-6, the surgical mesh and carrier assembly combination is preferably loosely folded prior to insertion into the first area portion of the package assembly. FIG. 4 illustrates an initial loose fold wherein the distal portions 400, 402 of the first area portion 220 of the carrier assembly are loosely folded (i.e., without forming hard creases) in toward the center. Subsequently, the second edges 216, 218 are loosely folded in toward the center, to result in the configuration shown in FIG. 6. The carrier assembly and mesh combination is then positioned within the container 710 adjacent the bottom side 714 of the container. As shown best in FIG. 7, the divider element 720 and instruments positioned thereon can then be inserted into the container.

Finally, the open top side of the container is subsequently covered and sealed with Tyvek® (not shown) to form a sealed blister container in a manner well known to those skilled in the art. This sealed container can then be sterilized by typical gas sterilization methods. As indicated previously, the mesh can readily be sterilized by this method even within the carrier assembly.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. A package assembly for surgical mesh comprising:
 a carrier assembly including a first substantially flat, flexible protective element having a periphery and positioned in a first plane, and a second substantially flat, flexible protective element having a periphery and positioned in a second plane parallel and substantially adjacent to the first plane; and
 a substantially flat, flexible surgical mesh having first and second sides and positioned between the first and second protective elements, the first and second protective elements being further dimensioned to cover the first and second sides of the surgical mesh respectively;
 wherein the first and second protective elements are joined together along at least a portion of their respective peripheries, but along no more of the periphery than that which will allow the first and second protective elements to be separated from one another to allow removal of the mesh by a user without separating the joined portion of their peripheries, and wherein the first protective element is comprised of a transparent or translucent material;
 wherein the peripheries of the first and second protective elements each include a first substantially straight edge, and wherein the first and second protective elements are joined together along the first edges;

wherein the peripheries of the first and second protective elements each define an area including a first area portion and a second area portion, wherein the first area portion is adjacent to the first edge, and the second area portion is adjacent to the first area portion and on an opposite side of the first area portion from the first edge, and wherein the first area portion has a width greater than that of the second area portion; and wherein the surgical mesh includes a first mesh portion having a first width and a second mesh portion having a second width less than the first width, and wherein the first mesh portion is positioned between the first area portions of the protective elements and the second mesh portion is positioned between the second area portions of the protective element.

2. The package assembly according to claim 1, wherein the peripheries of the first and second protective elements are substantially identical.

3. The package assembly according to claim 1, wherein the peripheries of the first and second protective elements each comprise a second substantially straight edge substantially parallel to the first side edge.

4. The package assembly according to claim 1, wherein the first and second protective elements are joined together only along their first edges.

5. The package assembly according to claim 1, wherein the first protective element is comprised of a copolymer polypropylene or polyester clear or translucent film.

6. The package assembly according to claim 5, wherein the second protective element is comprised of high density polyethylene.

7. The package assembly according to claim 1, wherein the surgical mesh is a mesh for pelvic floor repair.

* * * * *